United States Patent [19]

Danko et al.

[11] 4,343,190
[45] Aug. 10, 1982

[54] MOVING DIE RHEOMETER, METHOD OF TESTING MATERIALS THEREWITH, AND DIE FOR USE THEREIN

[75] Inventors: Michael J. Danko, Uniontown; Leslie L. Randall; Ray J. Smith, both of Akron; James E. Walsh, North Canton, all of Ohio

[73] Assignee: Monsanto Company, St. Louis, Mo.

[21] Appl. No.: 155,883

[22] Filed: Jun. 2, 1980

[51] Int. Cl.$^3$ .............................................. G01N 3/24
[52] U.S. Cl. ........................................ 73/846; 73/60; 73/860
[58] Field of Search ................. 73/60, 15.4, 15.6, 841, 73/842, 846, 54, 169, 150 R, 150 A, 815, 860

[56] References Cited

U.S. PATENT DOCUMENTS

| | | | |
|---|---|---|---|
| 2,704,451 | 3/1955 | Goeser | 73/846 X |
| 3,818,751 | 6/1974 | Karper et al. | 73/15.6 |
| 4,074,569 | 2/1978 | Sambrook et al. | 73/15.6 |
| 4,095,461 | 6/1978 | Starita | 73/15.6 X |

Primary Examiner—Kyle L. Howell
Assistant Examiner—Joseph W. Roskos
Attorney, Agent, or Firm—Gordon B. Seward

[57] ABSTRACT

The rheological properties of a viscoelastic material are measured by enclosing a sample of the material between two die members which have protrusions extending therefrom and intermeshing to form shear zones therebetween. The sample is sheared by displacing one member with respect to the other and the displacement force is measured.

A die is provided for the test, and means to bias the die members toward each other, to seal them together, to move one member with respect to the other and to measure the force required for such movement are provided.

39 Claims, 6 Drawing Figures

MOVING DIE RHEOMETER, METHOD OF TESTING MATERIALS THEREWITH, AND DIE FOR USE THEREIN

BACKGROUND OF THE INVENTION

This invention relates to measurement of the rheological properties of viscoelastic materials, and to an improved method and apparatus for such measurement. The invention is particularly applicable to the measurement of the rheological properties of vulcanizable elastomers as they are in the process of being vulcanized.

Prior art devices for measuring the rheological properties of viscoelastic materials include the device disclosed in U.S. Pat. No. 3,681,980. This device encloses a sample of material to be tested in a chamber under pressure, and subjects the sample to shearing forces by means of an oscillating rotor located in the chamber and surrounded by the sample. The torque generated in shearing the sample is displayed as a continuous curve, relating torque to time. By means of a heated chamber, the behavior of the sample is monitored as it is subjected to heat over a span of time. In the case of vulcanizable elastomers, a "cure curve" is thus obtained which can be valuable in predicting the behavior of the elastomer during processing and vulcanization.

A characteristic of such systems employing a rotor is that the rotor is not heated, hence accurate temperature control of the sample is difficult. Additionally, when the sample is in place the sample surrounds the rotor and thus it must be initially loaded in two segments. A sample which vulcanizes during testing must then be removed from around the rotor necessitating a time-consuming manual operation.

Efforts to design a "rotorless" device for measuring rheological behavior of elastomers have met with a number of difficulties. It has been found that unless the system is sealed the sample becomes porous, and test results are nonreproducible. Sealed systems often result in excessive friction in the seal area, thus contributing a substantial, variable component of the overall torque, with consequent erratic test results. Since the torque generated by the known rotorless devices is usually less than that of the rotor systems, the change for error can be further aggravated.

Edge effects are another problem with known rotorless die systems, wherein the outer edges of the sample, which are subjected to the highest shear forces, tend to break away from the die surfaces, causing sample slippage and giving erroneous results. If the angle of oscillation is reduced to avoid the edge-effect problem, torque values are correspondingly reduced and accuracy is further impaired. Any factor which lowers the ratio of actual shear torque to extraneous torque (similar to a "signal-to-noise" ratio) has a derogatory effect on the accuracy of the system.

Thus, a need exists for a system of measuring the rheological properties of viscoelastic materials which eliminates the rotor, yet gives accurate, reproducible test results.

BRIEF SUMMARY OF THE INVENTION

It is an object of this invention to provide a method for evaluating the rheological behavior of viscoelastic materials accurately and reproducibly, with a minimum of sample preparation, handling and removal. It is another object of this invention to provide a rotorless apparatus suitable for evaluating the rheological properties of a viscoelastic material sealed in a die which is capable of applying shear stress to the material and measuring the resistance thereto. It is a further object of this invention to provide a method and apparatus for evaluating accurately and quickly the cure characteristics of a vulcanizable elastomer.

These and other objects are accomplished by the instant invention which provides a method for testing viscoelastic material by substantially enclosing a sample of the material between two opposing die members which have protrusions extending from them between the members, the protrusions interlocking with each other to form shear zones between them; shearing the sample in the shear zones by displacing one die member with respect to the other; and measuring the force required for the displacement.

The invention also provides an apparatus for testing the rheological properties of a viscoelastic material including a die which has two opposing faces, annular wall means attached to at least one of the faces, and an annular seal in contact with the wall, the faces, wall and seal defining a closed space, and each face having protrusions which mesh with the protrusions from the other face; means to bias the faces together and to rotate one face with respect to the other; and means for measuring the rheological properties of a viscoelastic material contained in the die.

Viscoelastic materials are those substances which are plasticly deformable, and have both viscous and elastic properties. They include both natural and synthetic polymers whose viscosity characteristics are non-Newtonian, and encompass materials identified as plastics and rubbers. Of particular interest are elastomeric materials, both thermoplastic and thermosetting, and most particularly, vulcanizable elastomers, both synthetic and natural. The invention is especially useful in examining the rheological characteristics of vulcanizable elastomers during vulcanization.

In the method of the invention, a sample of the material to be tested is substantially enclosed between two opposing die members. Usually, a sample will be sized so as to completely fill the space between the two opposing die members, and it is preferable that a slight excess amount of sample is used, to insure that the space is filled. Conveniently, the die members are separated, and then brought back together after insertion of the sample between them. Any excess amount of sample can then escape through the closure area as the members are brought together. By "substantially enclosed" is meant that the die members may not completely enclose the sample, but that the sample is substantially surrounded on all sides by the two die members.

Preferably, the two die members are biased together, so as to exert pressure on the sample. One effect of biasing the die halves together is to enclose the sample more completely. Another related effect is that such a biasing action exerts a significant force on the sample so as to increase the frictional adhesion between the sample and the internal surfaces of the die members, thereby permitting the use of increased shearing force during the test over that which could be employed without such biasing action. Additionally, when the method is used to evaluate the rheological characteristics of vulcanizable elastomers, the use of biasing force on the die members is especially desirable. Most rubber compounds contain volatile materials which will produce porosity in the vulcanized rubber unless the vulcanization is performed under pressure. If such a rubber compound were tested according to the method of the invention, but without the pressure caused by biasing the die members together, the resultant porosity in the sample would give erroneous results. When the method of the invention is practiced with the optional step of biasing the die members together, it is possible to maintain an applied pressure on the sample, which may be kept constant or varied during the progress of the test. In order to maintain this pressure, the dies should preferably seal the sample between them. If one or both dies are slightly compliant, slight changes in sample volume during testing can be accommodated.

In the method of the invention, the die members feature protrusions extending into the space between them and interlocking with each other. By interlocking with each other is meant that the protrusion or protrusions from one die member extend beyond the plane of the protrusion or protrusions from the opposite die member. Stated another way, the opposing protrusions mesh with each other but do not touch each other. The function of these interlocking protrusions is to define between them shear zones, in which the sample is subjected to shearing forces by displacing one die member with respect to the other. The shear zones which are defined between the protrusions provide sufficient resistance to die displacement so as to enable the use of die-displacement forces of a magnitude previously unknown in rotorless rheometer designs, without slippage between the die surfaces and the sample. The total force is the integral of the local shear stress at each point on the die surface summed over the entire surface. Each of the shear zones acts to produce a contributing resistance, and the summation over the zones produces a total stress which opposes the die displacing force. Measurements of such force for different samples provide new standards by which the viscoelastic materials can be rated, giving an insight into their behavior during the processing steps normally encountered.

In order to maximize the shearing forces generated in the shear zones, it is preferred that the protrusions have faces which are generally parallel with one another, and that the displacement of the one die member be in a direction parallel with the faces. In this way, the forces in the shear zones are primarily shearing forces, rather than forces in tension or compression with respect to the sample. If the faces of the protrusions are in generally parallel planes, the die displacement can be performed so as to move one die toward and/or away from the other, or otherwise, so as to produce shearing forces in the shear zones.

In a preferred embodiment, the protrusions are annular and coaxial, and one die member is rotated with respect to the other. Thus, the protrusions take the form of concentric ring-like extensions from the die surfaces which mesh with one another to provide shear zones in the annular spaces between adjacent protrusions. While the walls of the protrusions can be smooth and regular, they can also have grooves, flutes or splines so as to decrease the likelihood of sample slippage. With such concentric arrangement, the rotation of the one die member is preferably an oscillating motion, with the moving die rotating back and forth through a relatively small angle, such as from 0.1 of a degree up to 10 degrees. The oscillating motion can be of a "sine wave" mode, with the speed of rotation varying from a minimum at each extreme of travel and passing through a maximum rotational velocity on its way to the other extreme. The frequency of the oscillation can vary from a relatively slow one cycle per minute up to as fast as 2000 cycles per minute. The desired frequency will depend on the rheological characteristics of the material being tested and the conditions of the test. Normally, the sample will be tested at a constant frequency, but, if desired, the frequency of oscillation can be varied throughout the test.

The protrusions produce another beneficial result in addition to their contribution to the total shear force. This result is concerned with control of the temperature of the sample. It is often desired to control sample temperatures during the test procedure, and in these instances it is usually desired to use temperatures above ambient. Higher test temperatures can simulate the elevated temperatures usually encountered in processing viscoelastic materials, such as in mixing, calendering, extrusion, and the like. More especially, when the vulcanization behavior of a vulcanizable rubber is being investigated, elevated sample temperatures are almost always essential. Because the protrusions provide a much greater surface area in relation to sample volume than previously obtained with rotorless rheometers, heat transfer to the sample is vastly improved, and control of sample temperatures is greatly facilitated. Both die members can be heated and temperature controlled, thus giving optimum control of the sample temperature during the test procedure.

In testing a sample of a viscoelastic material according to the method of the invention, the force required for displacing one die member with respect to the other can be measured over a period of time. The force can be measured by any convenient means, and can be continuously recorded over the test period. When vulcanizable elastomer samples are tested, the method of the invention can operate so as to evaluate the vulcanization behavior of the sample with time. A so-called "cure curve" can be generated, to show the time rate of the increase in force as the vulcanization reaction proceeds. By testing known rubber compounds at reference temperatures, standard cure curves can be generated by which to measure the effect of changes in rubber compound formulations. Thus, the method can serve as a production control test, and also as a laboratory tool for investigating the effect of changes in compound formations or the use of new polymers.

The invention also features a novel die adapted to apply shear stress to a sample of viscoelastic material contained therein, comprising two opposing die faces and annular wall means attached to at least one of the faces, the faces and wall means defining a closed space. Each face has at least one annular protrusion extending from it toward the opposite face, and the annular protrusion or protrusions from one face interlock with the annular protrusion or protrusions from the other face. Annular sealing means are included, in contact with the wall means. The sealing means can be an O-ring. The annular wall means and protrusions can be coaxial, and the die faces can be parallel with each other. In a preferred mode, the annular protrusions are hollow cylinders, perpendicular to the die faces and parallel with each other. The surfaces of the cylinders need not be smooth, however, and can be grooved or fluted so as to increase the resistance to slippage between die and sample under shearing forces.

Sealing means is provided in contact with the wall means, at the point where the two faces would otherwise come into contact with each other. As explained above, a desirable seal means is one which will contain the sample to be tested between the die faces with a minimum amount of friction at the point of contact when one die face is displaced with respect to the other. The seal can take the form of a knife edge which extends from the wall means and over the edge of the opposing die face, so that the force biasing the die halves together keeps the knife edge in contact with the die face, preserving the integrity of the seal.

Alternatively, as mentioned above, the seal can incorporate a resilient deformable member such as a gasket made from an elastomeric material, such as rubber. Silicone rubber or a fluorocarbon elastomer can be employed for such purpose, combining flexibility, resilience, heat resistance, and low friction. When an annular die is used, the gasket can take the form of an O-ring.

Advantageously, one or both of the die faces can be so constructed as to distort slightly under internal pressure. If one or both die faces are compliant, so as to "bow out" under internal pressure, the sample can be maintained under a relatively constant pressure through the duration of the test even if changes in sample volume occur. Such a compliant die face, or faces can be made from a resilient metal of such thickness that a slight outward deflection will occur under the internal pressures employed.

Spacing of the annular protrusions can be such as will assure a relatively even distribution of shearing forces across the die faces. Since the radially outer die portions travel proportionally farther than the inner die portions during rotation, the outermost die portions would tend to be subjected to the greatest shearing forces. In order to equalize the shearing forces across the die faces, the protrusions are preferably spaced so as to have narrower shear zones between adjacent protrusions near the center of the die, and wider shear zones at or near the periphery of the dies. By employing this design feature, the situation can be avoided wherein local shearing forces at the die peripheries are so great as to cause local separation between the die and the sample, with resultant erroneous test values.

Rotation of one die member with respect to the other can be accomplished by means of any known mechanism to provide rotating, preferably reciprocating motion. An electric motor coupled to the appropriate gearing can suffice for this purpose.

Measurement of the force required for rotating the one die face with respect to the other can be accomplished in any convenient manner. A torque transducer can be employed which will supply an output signal proportional to the force. The signal can be then treated in any convenient manner so as to reflect the shearing forces on the sample at any time.

The die faces are separable for easy insertion and removal of the samples, and, during the testing procedure, are biased together with a controllable force. Such biasing force can be supplied by any known biasing means, such as a spring, fluid pressure device, weight, and the like. Fluid pressure is most advantageously used as providing accurate control of pressure as well as a continuous indication of the degree thereof. An air cylinder is effective for this purpose, and can supply such force as is normally used in vulcanizing rubber under pressure.

The die of the invention can be utilized in apparatus for testing rheological properties of viscoelastic materials in combination with means for rotating one of the die faces with respect to the other and means to measure the rheological properties of a viscoelastic material contained in the die.

A more complete understanding of the invention can be obtained by reference to the drawings and to the description of preferred embodiments following.

DETAILED DESCRIPTION

Figure 1:
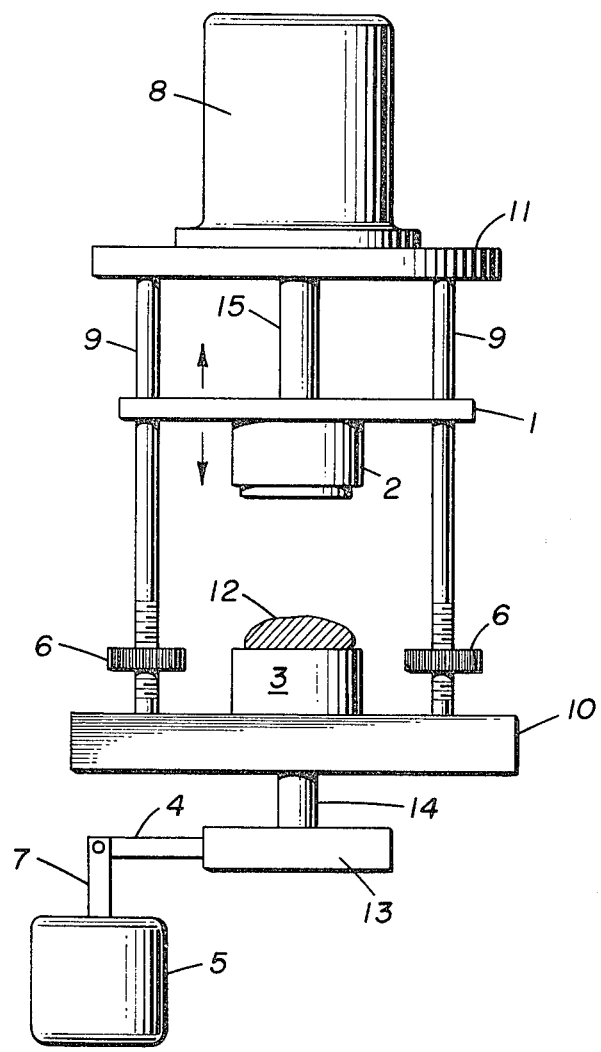
FIG. 1 is a front elevation depicting an overall view of the apparatus.

Referring to FIG. 1, a preferred embodiment of the apparatus of the invention is shown. Upper support member 11 is rigidly connected to lower support member 10 by guide rods 9. An air cylinder is mounted on upper support member 11 and its drive piston 15 is connected to crosshead 1, on which is mounted upper die half 2. A pressure transducer (not shown) is incorporated in the cylinder mechanism to provide signals indicative of the applied pressure. Actuation of the air cylinder 8 causes up and down motion of crosshead 1, which slides on guide rods 9. Crosshead travel is limited by adjustable stops 6, threaded onto guide rods 9. Lower die half 3 is based on lower support 10. Drive shaft 14 is attached to lower die half 3 through the lower support 10, and is attached to drive system 13 which contains a thrust bearing and a shaft coupling. Shaft 14 is driven by variable speed drive motor 5 through eccentric 7 and drive system 13 to provide oscillating movement of lower die half 3. A torque transducer 4 provides a signal indicative of the torque at any instant.

Operation of the device of FIG. 1 begins with placement of a cold (room temperature) test sample 12 on lower die half 3. Air cylinder 8 is then actuated to move piston 15 downward so as to move crosshead 1 and upper die half 2 downward until crosshead 1 contacts stops 6. At this point, the two die halves have come together, enclosing sample 12 between them. Oscillatory motion is being continually applied to the lower die half during closing, and the sample is brought to the desired testing temperature by heating elements (not shown) in each die half. This motion is accomplished by the combined action of drive motor 5, eccentric 7, and drive system 13, so as to oscillate lower die half 3. Since upper die half 2 is stationary, relative oscillation between the two die halves acts to apply shear stress on sample 12. The output signal from torque transducer 4 is suitably conditioned and displayed by electronic equipment (not shown) to yield rheological data on the sample. At completion of the test, the piston 15 and crosshead 1 are raised, opening the die. The sample may then be removed, and the system is ready for introduction of the next sample to be tested.

Figure 2:
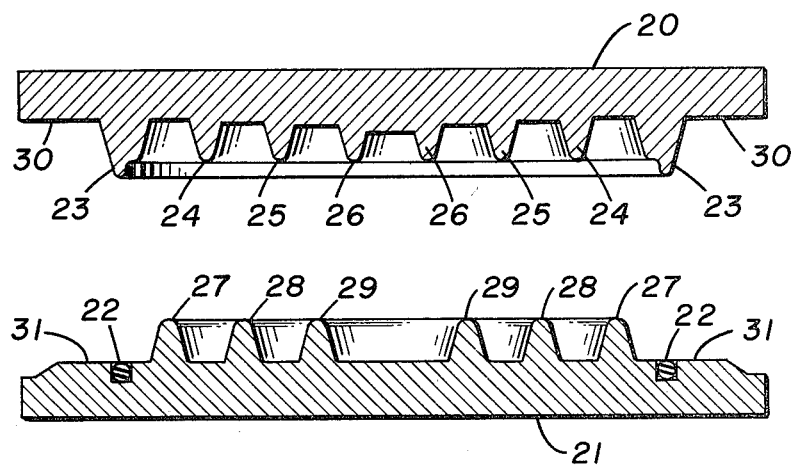
FIG. 2 is a sectioned detail view showing both die halves in an open position.

Referring to FIG. 2, a preferred embodiment of the die of the invention is depicted, including cross-sections of both upper and lower die halves. The die is shown in an open position, with no sample present.

Upper die half 20 has annular protrusions 24, 25 and 26 which extend downward from the upper die face 30. Annular wall 23 also extends downward from the upper die face 30.

Similarly, lower die half 21 has annular protrusions 27, 28, and 29 extending upward from lower die face 31. O-ring 22 is carried on the face 31 of lower die half 21.

Figure 3:
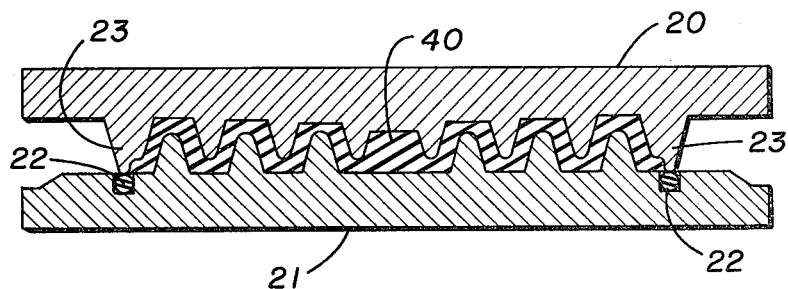
FIG. 3 is a sectioned detail view, similar to FIG. 2, but with the die in the closed position, and a sample in place.

FIG. 3 shows a preferred embodiment of the die as shown in FIG. 2. In FIG. 3, however, the upper and lower die halves have been moved together, and an elastomer sample is contained between them. The protrusions (unnumbered) from upper die face 20 extend beyond those from lower die face 21. Elastomer sample 40 occupies the space defined by the two die halves. The annular wall 23 is in sealing contact with O-ring 22.

Figure 4:
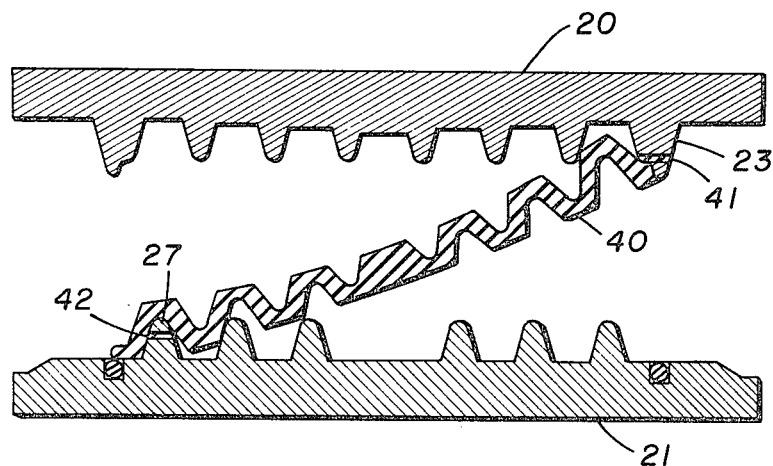
FIG. 4 is a sectioned detail view, similar to FIGS. 2 and 3, but showing a sample being removed.

Referring to FIG. 4, upper and lower die halves are shown with a sample in partial engagement with both halves. Upper die half 20 has a small hole 41 through the annular wall 23. Similarly, lower die half 21 has a small hole 42 through outer annular protrusion 27, located opposite from hole 41. As the die halves are separated, sample 40 is temporarily held by the small "arms" of material which adhere to each hole, and the sample can thus be easily removed. Mechanical means may be used to complete removal of the tested sample, since it will be suspended between the upper and lower die halves, and not wholly held by either die half.

Figure 5A:
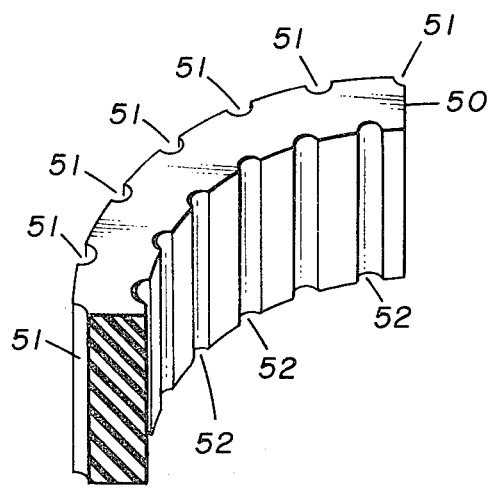
FIGS. 5A and 5B are sectioned perspective views showing annular protrusions having flutes and splines, respectively, on their surfaces.
Figure 5B:
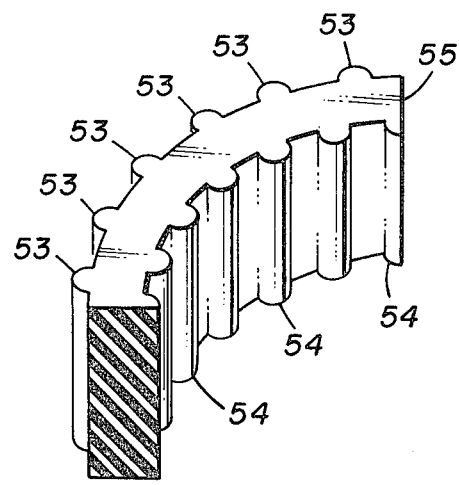

In FIGS. 5A and 5B, annular protrusions are shown which feature flutes and splines, respectively, on the walls of the protrusions. As shown, the flutes and splines are oriented parallel to the axes of the annular protrusions, however, they could be oriented otherwise, as, for example, circumferentially with respect to the annular protrusions. The axial orientation of the flutes or splines produces maximum resistance to sample slippage and little difficulty in removing the sample from the mold at the conclusion of the test.

Referring to FIG. 5A, a portion of an annular protrusion having flutes is shown in perspective view. Flutes 51 are shown in the radially outer surface of protrusion 50, and flutes 52 in the radially inner surface.

Similarly, FIG. 5B shows a portion in perspective view of an annular protrusion which has splines on its surfaces. Splines 53 are shown on the radially outer surface of protrusion 55, and splines 54 on the radially inner surface.

Although the invention has been illustrated by typical examples, it is not limited thereto. Changes and modifications of the examples of the invention herein chosen for purposes of disclosure can be made which do not constitute departure from the spirit and scope of the invention.

The embodiment of the invention in which an exclusive property or privilege is claimed are defined as follows:

1. The method of testing a viscoelastic material comprising the steps of
    substantially enclosing a sample of the material between two opposing die members having protrusions extending therefrom between the members, which protrusions interlock to form shear zones therebetween,
    shearing the sample in the shear zones by displacing one die member with respect to the other, and
    measuring the force required for such displacement.
2. The method of claim 1, wherein the protrusions have faces generally parallel with one another, and the displacement is in the direction parallel with the faces.
3. The method of claim 1, wherein the dies are biased together, thereby exerting pressure on the sample.
4. The method of claim 3, wherein the pressure on the sample is continuously measured and controlled.
5. The method of claim 3, wherein the sample is sealed between the die halves.
6. The method of claim 3, wherein variations in sample volume are accomodated by flexing of at least one die member.
7. The method of claim 1, wherein the temperatures of the die members are controlled at a desired level.
8. The method of claim 1, wherein the protrusions are annular and coaxial, and the one die member is rotated with respect to the other.
9. The method of claim 8, wherein the one die member is rotated in an oscillating motion.
10. The method of claim 9, wherein the one die member is oscillated through an angle of from 0.1° to 10°.
11. The method of claim 9, wherein the one die member is oscillated in a sine wave motion.
12. The method of claim 9, wherein the one die is oscillated at a frequency of from one to 2000 cycles per minute.
13. The method of claim 12, wherein the frequency is changed during the test.
14. Apparatus for testing rheological properties of viscoelastic material comprising, in combination, a die having two opposing faces and annular wall means attached to at least one of said faces, annular sealing means arranged to contact said wall means, said faces wall means and sealing means defining a closed space, each face having at least one annular protrusion extending therefrom toward the opposing face, the annular protrusions from one face intermeshing with the annular protrusions from the opposing face, means biasing said faces towards one another, means for rotating one of said faces with respect to the other, and measuring means for measuring rheological properties of a viscoelastic material contained in said die.
15. Apparatus of claim 14, wherein said wall means and said annular protrusions are coaxial.
16. Apparatus of claim 14, wherein said faces are generally parallel with each other.
17. Apparatus of claim 14, wherein said faces are heated and temperature controlled.
18. Apparatus of claim 14, wherein said annular protrusions comprise hollow cylinders.
19. Apparatus of claim 18, wherein said protrusions have grooves, flutes or splines.
20. Apparatus of claim 14, wherein each of said faces has two annular protrusions extending therefrom.
21. Apparatus of claim 14, wherein each of said faces has three annular protrusions extending therefrom.
22. Apparatus of claim 14, wherein said annular sealing means comprises an O-ring.
23. Apparatus of claim 22, wherein said O-ring is made from a fluorocarbon elastomer.
24. Apparatus of claim 14, wherein said biasing means comprises a fluid pressure device.
25. Apparatus of claim 24, wherein said fluid pressure device is an air cylinder.
26. Apparatus of claim 24, wherein said fluid pressure device is adapted to maintain a constant pressure within said die.
27. Apparatus of claim 24, wherein said fluid pressure device includes a pressure transducer.

28. Apparatus of claim 14, wherein said rotating means is adapted to rotate said one face through an angle of up to 15°.

29. Apparatus of claim 14, wherein said rotating means is adapted to oscillate said one face.

30. Apparatus of claim 29, wherein said rotating means is adapted to oscillate said one face in a sine wave pattern.

31. Apparatus of claim 14, wherein said measuring means is adapted to measure the force required to rotate said one face.

32. Apparatus of claim 31, wherein said measuring means comprises a torque transducer.

33. In a die adapted to apply shear stress to a sample of viscoelastic material contained therein, comprising, in combination, two opposing faces, annular wall means attached to at least one of said faces and annular sealing means arranged to contact said wall means, the improvement wherein each of said faces has at least one annular protrusion extending therefrom toward the opposing face, the annular protrusions from one face intermeshing with the annular protrusions from the opposing face.

34. The die of claim 33, wherein the wall means and the annular protrusions are coaxial.

35. The die of claim 33, wherein the faces are parallel with each other.

36. The die of claim 33, wherein the annular protrusions comprise hollow cylinders.

37. The die of claim 36, wherein a hole is provided through at least one of said annular protrusions.

38. The die of claim 37, wherein the annular sealing means comprises an O-ring.

39. The die of claim 33, wherein the wall means and the protrusions are generally perpendicular to the faces.

* * * * *